United States Patent
Campbell et al.

(10) Patent No.: US 6,270,527 B1
(45) Date of Patent: Aug. 7, 2001

(54) ELASTIC VALVE WITH PARTIALLY EXPOSED STENT

(75) Inventors: Louis A. Campbell; Riyad Moe, both of Austin, TX (US)

(73) Assignee: Sulzer Carbomedics Inc., Austin, TX (US)

( * ) Notice: Subject to any disclaimer, the term of this patent is extended or adjusted under 35 U.S.C. 154(b) by 0 days.

(21) Appl. No.: 09/174,387

(22) Filed: Oct. 16, 1998

(51) Int. Cl.⁷ ........................................................ A61F 2/24
(52) U.S. Cl. ............................................. 623/2.18; 623/900
(58) Field of Search ................................ 623/900, 2.12, 623/2.14, 2.17, 2.18

(56) References Cited

U.S. PATENT DOCUMENTS

| | | | |
|---|---|---|---|
| 4,297,749 | * | 11/1981 | Davis et al. .......................... 623/2.12 |
| 4,605,407 | * | 8/1986 | Black et al. .......................... 623/2.12 |
| 5,411,552 | * | 5/1995 | Andersen et al. .................... 623/2.12 |
| 5,489,297 | * | 2/1996 | Duran .................................. 623/2.12 |
| 5,545,215 | * | 8/1996 | Duran .................................. 623/2.12 |
| 5,855,597 | | 1/1999 | Jayaraman ............................... 623/1 |
| 5,855,601 | * | 1/1999 | Bessler et al. ........................ 623/2.12 |
| 6,027,525 | * | 2/2000 | Suh et al. ............................. 623/2.12 |

FOREIGN PATENT DOCUMENTS

| | | |
|---|---|---|
| 0 850 607 A1 | 1/1998 | (EP) . |
| WO 97/19655 | 5/1997 | (WO) . |

\* cited by examiner

*Primary Examiner*—Bruce Snow
(74) *Attorney, Agent, or Firm*—Kenneth S. Barrow; Philip S. Lyren; Timothy L. Scott (57) ABSTRACT

A valve includes an elastic valve body and a stent. A first portion of the stent is embedded in the elastic valve body and a second portion of the stent is outside the valve body. A method of manufacturing such a valve is also claimed.

11 Claims, 7 Drawing Sheets

ELASTIC VALVE WITH PARTIALLY EXPOSED STENT

TECHNICAL FIELD

The present invention pertains to valves and in particular to tri-leaflet heart valve prostheses.

BACKGROUND OF THE INVENTION

Ever since 1950, when blood oxygenators made open heart surgery feasible, it has been possible to treat some forms of heart disease by replacing one of the patient's heart valves with a prosthetic valve. Early heart valve prostheses included ball-and-cage valves and disc-and-cage valves in which a ball or a disc was housed in a cage. One side of the cage provided an orifice through which blood flowed either into or out of the heart, depending on the valve being replaced. When blood flowed in a forward direction, the energy of the blood flow forced the ball or disc to the back of the cage allowing blood to flow through the valve. When blood attempted to flow in a reverse direction, or "regurgitate", the energy of the blood flow forced the ball or disc into the orifice in the valve and blocked the flow of blood.

A bi-leaflet valve comprised an annular valve body in which two opposed leaflet occluders were pivotally mounted. The occluders were typically substantially rigid, although some designs incorporated flexible leaflets, and moved between a closed position, in which the two leaflets were mated and blocked blood flow in the reverse direction, and an open position, in which the occluders were pivoted away from each other and did not block blood flow in the forward direction. The energy of blood flow caused the occluders to move between their open and closed positions.

A tri-leaflet valve comprised an annular valve body in which three flexible leaflets were mounted to a portion of the valve body, called a "stent," located at the circumference of the annulus. Some tri-leaflet valves used rigid leaflets. When blood flowed in the forward direction, the energy of the blood flow deflected the three leaflets away from the center of the annulus and allowed blood to flow through. When blood flowed in the reverse direction, the three leaflets engaged each other in a coaptive region, occluded the valve body annulus and prevented the flow of blood. The valve leaflets were made from tissue, such as specially treated porcine or bovine pericardial tissue or from a man-made material such as polyurethane or another biocompatible polymer.

A heart valve is implanted into an annular opening in a heart created when the diseased valve is removed. The valve can be secured in the annulus through the use of sutures or pins that penetrate the host tissue and an outside edge of the valve. Alternatively, a sewing ring can be attached, typically with sutures, to the elastic valve. The valve can then be secured in the annulus by suturing the host tissue to the sewing ring.

An important consideration in prosthetic heart valve design is the durability of the heart valve. Replacing a prosthetic heart valve after it has been implanted is dangerous and expensive for the patient and failure of a prosthetic heart valve can cause the death of a patient. One source of prosthetic heart valve failure is tearing of the elastic material that forms the heart valve.

SUMMARY OF THE INVENTION

The invention improves the durability of elastic heart valves by eliminating the need to pierce the elastic material of the heart valve during construction of the sewing ring or during implantation.

In general, in one aspect, the invention features a valve comprising an elastic valve body and a stent, a first portion of the stent being embedded in the elastic valve body and a second portion of the stent being outside the valve body.

The invention may include one or more of the following. A sewing ring may be coupled to the second portion of the stent. The coupling may be provided by sutures. The coupling may be provided by a cloth. A coupling element may be coupled to the second portion of the stent and the sewing ring may comprise sewing ring fabric. The sewing ring may be coupled to the coupling element by wrapping the sewing ring fabric around the second element. The valve body may comprise an embedding layer for embedding the first portion of the stent. The embedding layer may comprise a first portion for embedding a peak of the stent and a second portion for embedding a base of the stent. The valve body may comprise silicon. The valve body may comprise an elastic material and the stent may be encapsulated by the elastic material of the valve body. The stent may be insert molded into the valve body. The valve body may comprise molded features that mechanically capture the stent.

In general, in another aspect, the invention features a valve comprising an elastic valve body, a stent engaged with the valve body, a sewing ring, and a coupling between the sewing ring and the stent.

In general, in another aspect, the invention features a method for manufacturing a valve comprising forming a valve body from elastic material, embedding a first portion of a stent in the elastic material, and leaving outside the elastic material a second portion of the stent.

DESCRIPTION OF THE PREFERRED EMBODIMENTS

Figure 1:
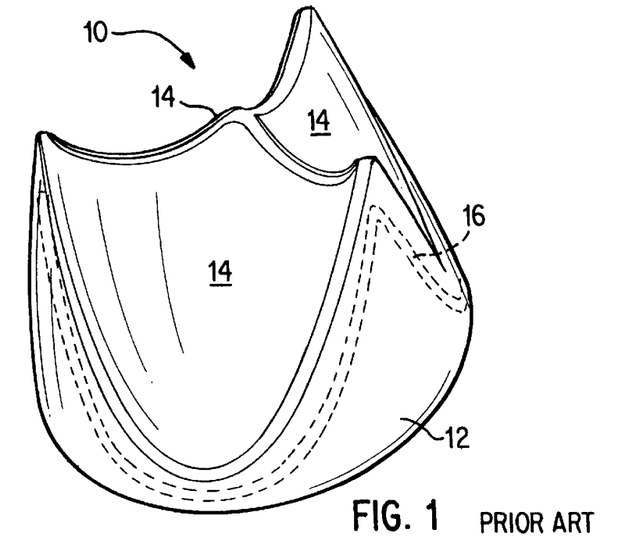
FIG. 1 is a perspective view of a prior art elastic valve.

A tri-leaflet heart valve 10 comprises an annular elastic valve body 12 and three flexible leaflets 14 made of a biocompatible polymer such as silicone or polyurethane, as shown in FIG. 1. A flexible stent 16, made of metal or plastic, reinforces the elastic valve body. In prior art valves, the flexible stent 16 was embedded in the elastic material that formed the valve body 12, as shown in FIG. 1.

Figure 2:
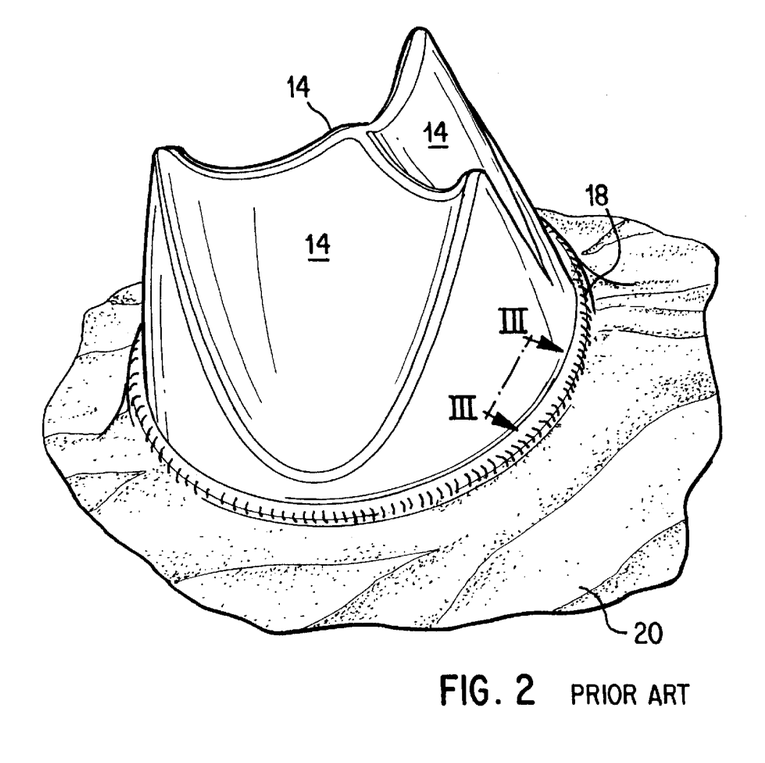
FIG. 2 is a perspective view of a prior art elastic valve implanted into tissue.
Figure 3:
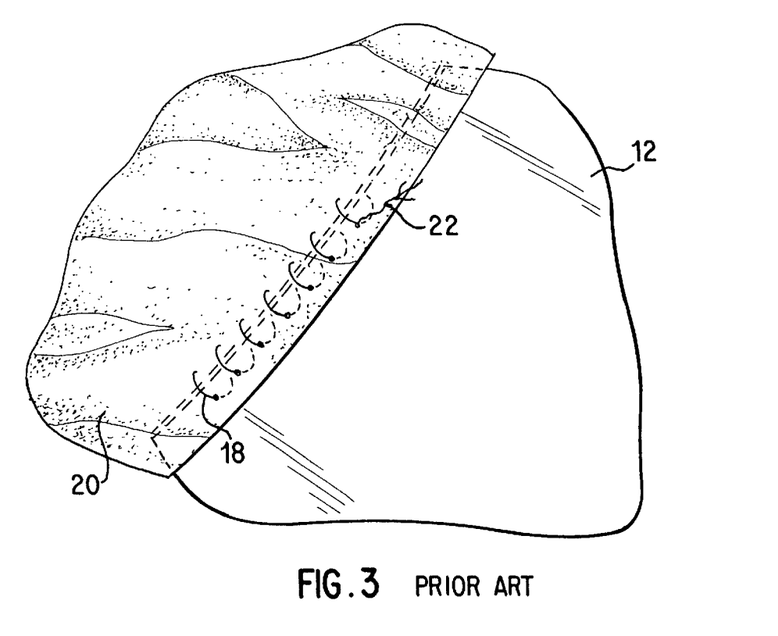
FIG. 3 is a view of a prior art elastic valve along lines III of FIG. 2.

In some prior art designs, sutures or pins 18 were placed through an outside edge of the valve body 12 for attachment of the valve to the host tissue 20 as shown in FIG. 2. The needle holes in the valve body 12 through which the sutures 18 or pins pass are locations for crack 22 initiation, as shown in FIG. 3. Analysis has shown that cracks 22 can emanate from the suture 18 or pin holes and propagate into the leaflets 14. Such propagation will lead to incompetence of the leaflet and eventual structural failure of the leaflet 14.

Figure 4:
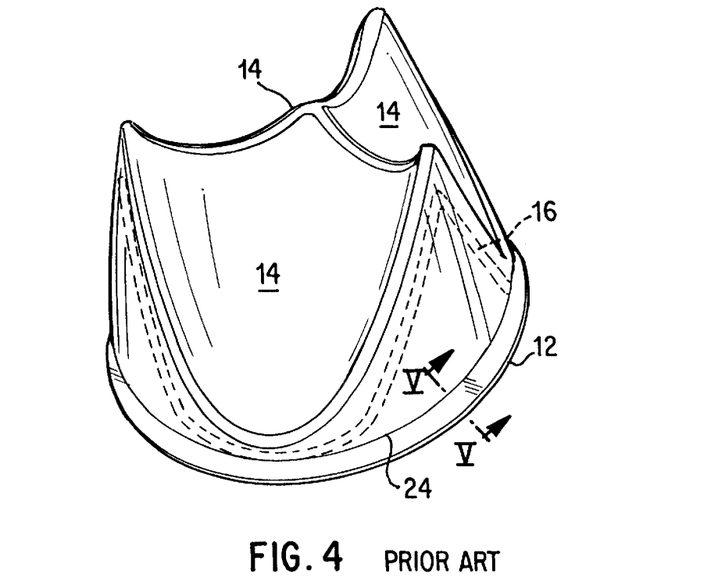
FIG. 4 is a perspective view of a prior art elastic valve.
Figure 5:
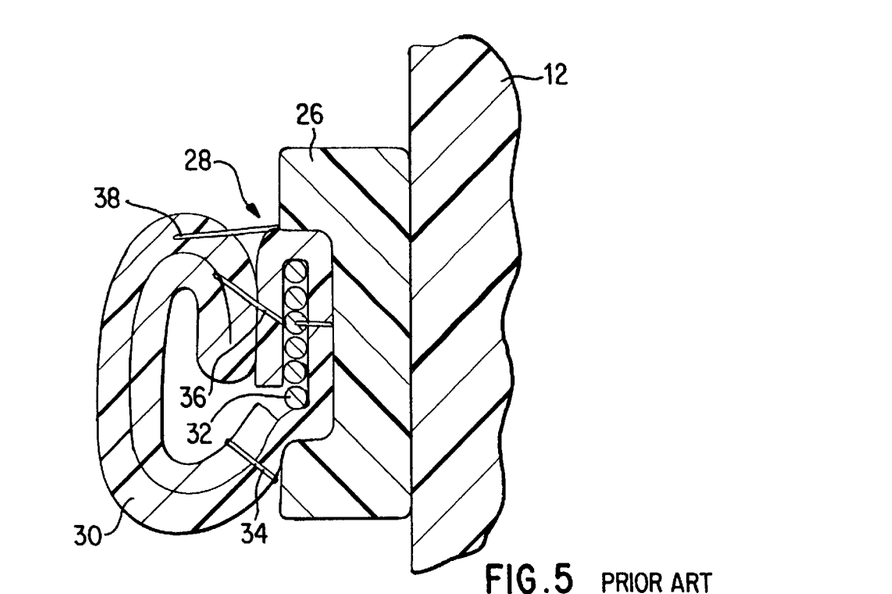
FIG. 5 is a view of a prior art elastic valve along lines V of FIG. 4.
Figure 6:
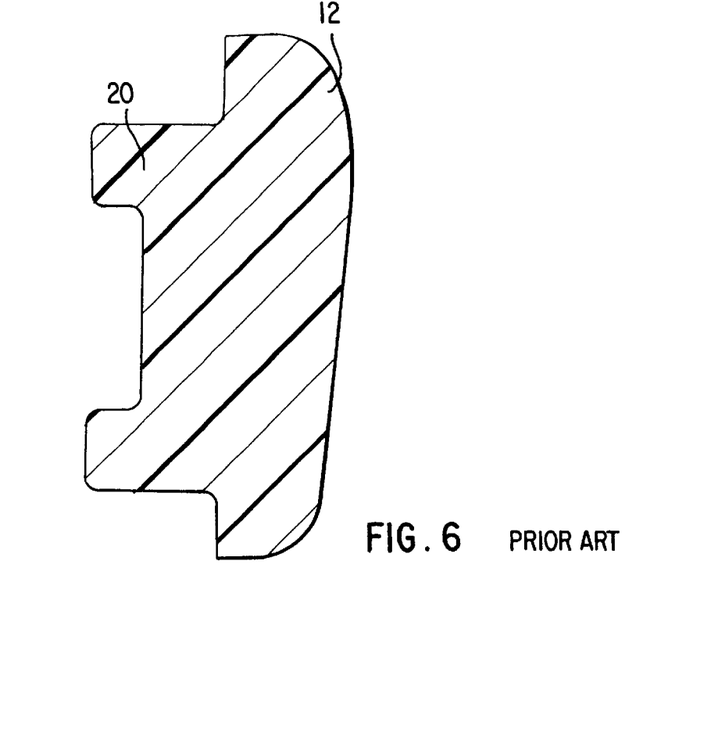
FIG. 6 is a view of a portion of a prior art elastic valve along lines V of FIG. 4.

In some prior art designs, a sewing ring 24 was coupled to the valve body 12, as shown in FIG. 4. The sewing ring 24 provided a point to attach the valve body 12 to heart tissue 20. The coupling is sometimes provided by a metal or plastic ring 26, which fits around the outside diameter of the valve body 12, as shown in FIG. 5. The ring 26 may be separate from the valve body 12, as shown in FIG. 5, or it may be part of the valve body, as shown in FIG. 6. The ring 26 includes a groove 28 on the side opposite the side of the ring 26 adjacent the valve body 12. A sewing cuff 30 is coupled to the ring 26 by a suture windings 32 which wrap around the ring 26 and draw the sewing cuff 30 into the groove 28 on the ring or valve body. Additional sutures 34, 36 and 38 are added to form the sewing cuff 30 into its final shape, shown in FIG. 5.

In coupling devices such as that shown in FIG. 5, the valve body or ring 26 have to be stiff or they will deform allowing the sewing ring 24 to come off the valve. If the valve body or ring 26 are not sufficiently rigid, the compressive forces placed on them when the sutures 32 are tied tightly down around the ring will crush them. The addition of a ring 26 will also make the valve thicker, thus reducing the available flow area. Further, with the type of construction illustrated in FIG. 5, it is difficult to have a scalloped sewing ring that includes axial changes in the location of the ring at different rotational positions. The native annulus in the heart has this type of scalloping, as do tissue valves, which makes a scalloped inflow a desirable characteristic. Finally, the type of construction illustrated in FIG. 5 allows the sewing ring to come off the valve if the sutures 32 securing the sewing cuff 30 to the valve body or ring 26 are cut, which is a reported failure mode for valves employing this kind of construction.

Figure 7:
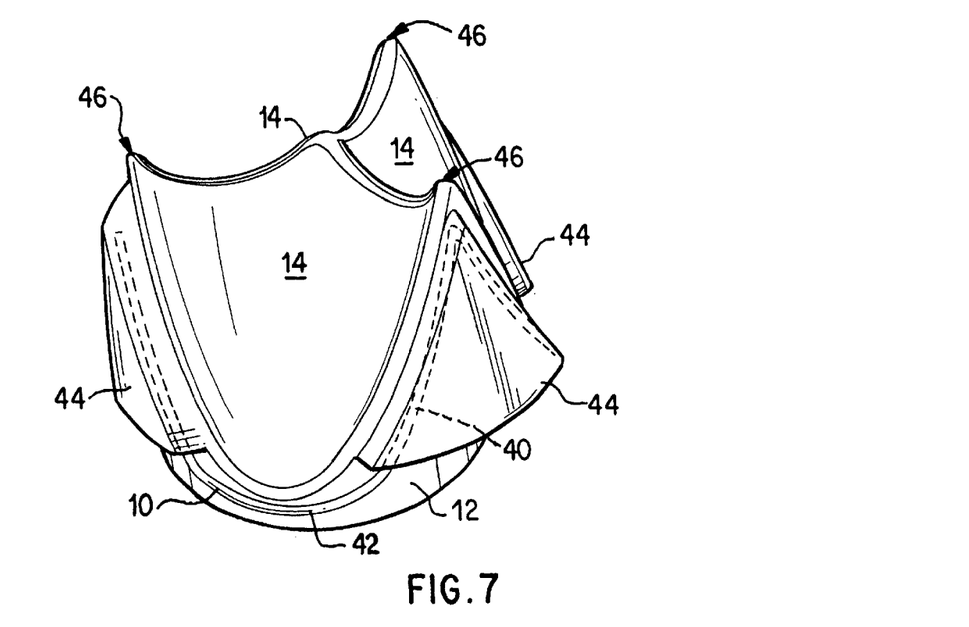
FIG. 7 is a view of an elastic valve according to the present invention.

The invention provides a coupling between the heart tissue 20 and the valve body 12 that does not require the valve body to be pierced and which does not use a ring of the sort illustrated in FIG. 5. This is accomplished by providing a stent 16, a first portion 40 of which is embedded in the valve body 12 and a second portion 42 of which is outside the valve body 12, as shown in FIG. 7. An embedding layer 44 is added to an outside surface of the valve body 12 near each of the three locations where two leaflets come together near the inside surface of the valve, or "commissure" 46. The first portion 40 (which is in three segments) of the stent is embedded in the embedding layer 44 of the valve body 12. The second portion 42(which is in three segments) of the stent is outside the embedding layer 44.

Figure 8:
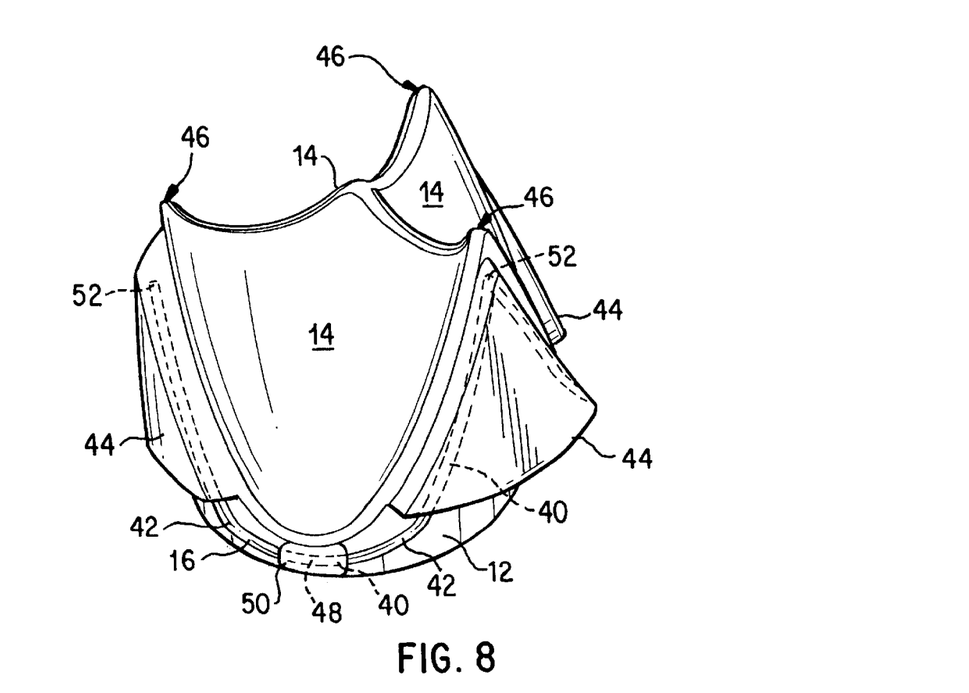
FIG. 8 is a view of an elastic valve according to the present invention.

In another embodiment, illustrated in FIG. 8, the bases 48 of the stent are embedded in a base embedding layer 50, which is added to the outside surface of the valve body 12. The peaks 52 of the stent are embedded in the embedding layer 44. In this embodiment, the first portion 40 of the stent, which is embedded in the embedding layer or the base embedding layer, is in six segments. The second portion 42 of the stent, which is outside the embedding layer and the base embedding layer, is also in six segments.

Figure 9:
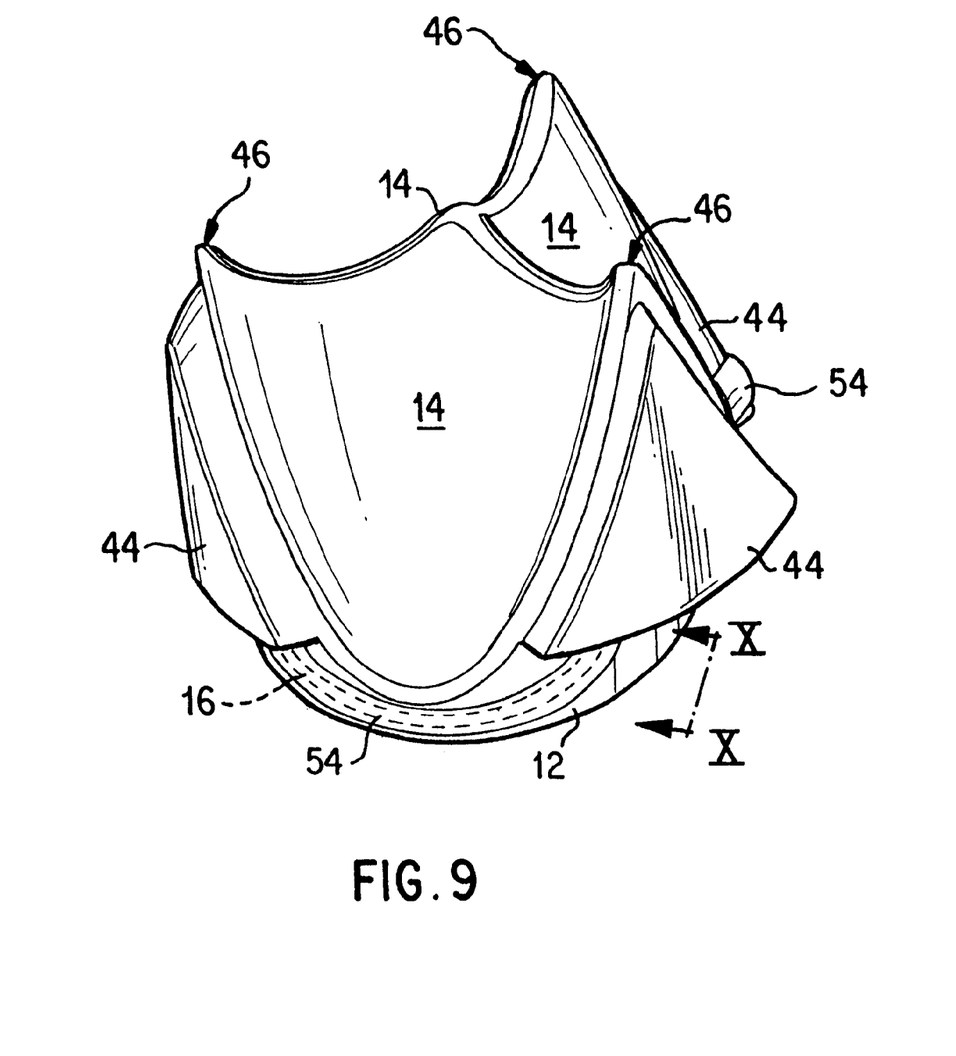
FIG. 9 is a view of an elastic valve according to the embodiment of the present invention.

A sewing ring 54 can be added to the valve body 12 as shown in FIG. 9. The sewing ring 54 attaches to the second portion 42 of the stent 16 in the regions where the stent 16 is outside the elastic material of the valve body 12. In the regions where the stent is embedded in the embedding layer 44 the sewing ring falls below the embedding layer 44.

Figure 10:
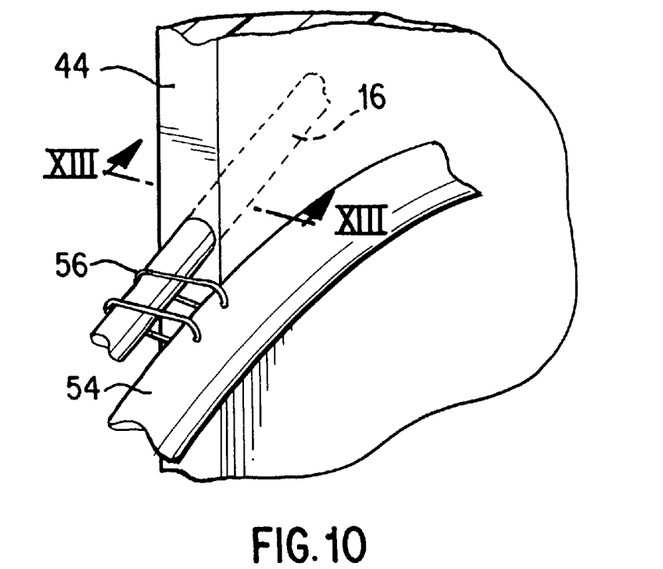
FIG. 10 is a view of a portion of an elastic valve according to the embodiment of the present invention of FIG. 9.
Figure 11:
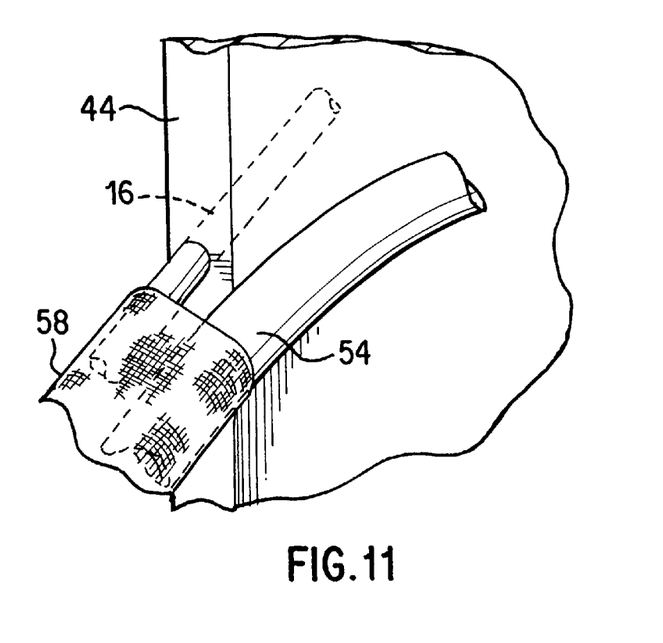
FIG. 11 is a view of a portion of an elastic valve according to the embodiment of the present invention of FIG. 9.

This configuration allows the sewing ring 54 to be coupled to the valve body 12 without the necessity of piercing the valve body 12 with sutures or pins and without the need for a groove in the valve body or ring, as shown in FIGS. 10 and 11. In FIG. 10, the coupling between the sewing ring 54 and the stent 16 is provided by sutures 56 that wrap around the stent 16 and pass through the sewing ring 54. The sutures 56 do not pass through the embedding layer 44 or any other part of the valve body 12. In the region where the sutures 56 are absent, the sewing ring 54 is press fit against the valve body 12.

The sewing ring is firmly coupled to the valve body because the stent is embedded in the valve body and cannot slip loose. Further, the coupling between the sewing ring and the stent is provided by individual sutures that do not place any compressive force on the stent. Because the stent is already present in the valve body, the coupling between the sewing ring and the stent does not add any thickness to the valve, leaving the flow area unaffected. Further, the sewing ring is only fixed where it is attached to the stent. In other areas it can follow the scalloping of the native heart tissue. Finally, if a suture coupling the sewing ring to the stent is cut, the remaining sutures will keep the sewing ring firmly attached to the stent and thereby to the valve body.

In FIG. 11, the coupling is provided by cloth 58 that wraps around the stent 16 and the sewing ring 54. The cloth 58 stops at the edge of the embedding layer 44. Again, in the region where the cloth is not present, the sewing ring 54 is press fit against the valve body 12.

Figure 12:
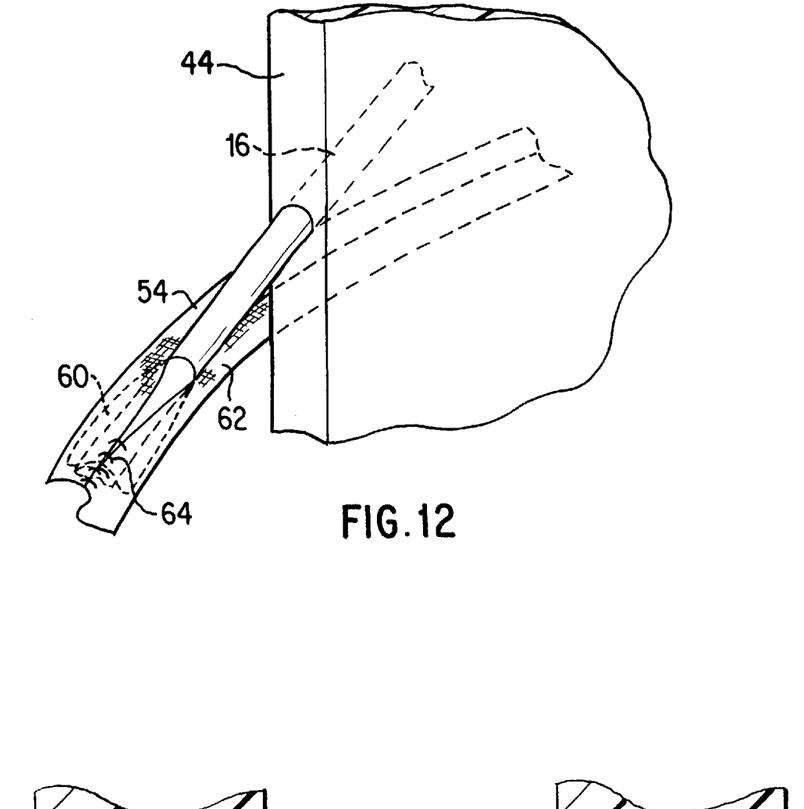
FIG. 12 is a view of a portion of an elastic valve of another embodiment of the invention.

In FIG. 12, an elastic element 60 is insert molded around the exposed portion of the stent 16. Sewing ring fabric 62 is wrapped around the elastic element 60 and secured by sutures 64, which makes the elastic element 60 the filler for the sewing ring for the exposed portion of the stent 16. Again, in the region where the stent is not exposed, the sewing ring 54 is press fit against the valve body 12. The sutures that secure the valve to the heart tissue pass through the sewing ring fabric 62 and the elastic element 60. The elastic element 60 is separate from the valve body 12 so that any cracks that form in the elastic element 60 because of the sutures will not propagate into the valve body 12.

Figure 13:
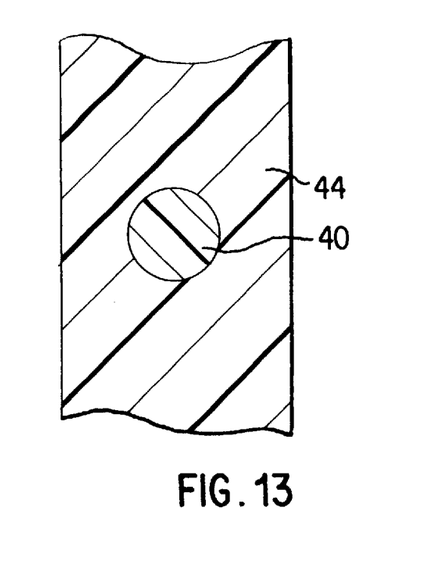
FIG. 13 is a section view of a portion of an elastic valve along lines XIII of FIG. 10.
Figure 14:
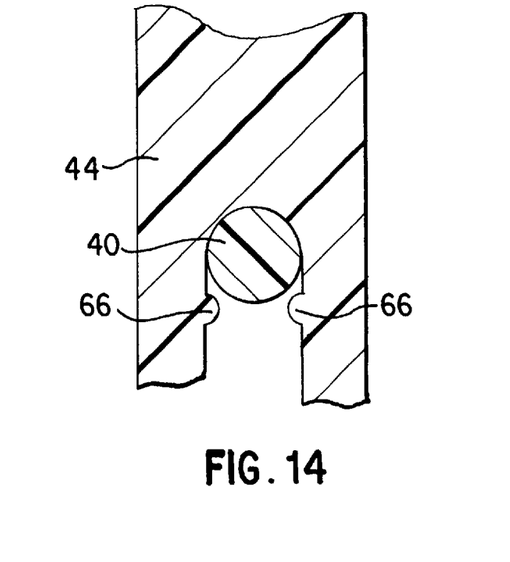
FIG. 14 is a section view of a portion of an elastic valve along lines XIII of FIG. 10.

A valve body according to the present invention can be manufactured by encapsulating the first portion 40 of the stent 16 in elastic material, as shown in FIG. 13, during dip casting of the valve body 12. Alternatively, the valve body 12 can be manufactured with capture features 66 molded into the embedding layer 44, as shown in FIG. 14. After the molding process is completed, the stent 16 can be pressed into the embedding layer 44 of the valve body where the capture features 66 mechanically capture it. Other alternatives include insert, compression or transfer molding the stent 16 into the embedding layer 44.

The foregoing describes preferred embodiments of the invention and is given by way of example only. For example, the invention is not limited to the manufacturing techniques disclosed but includes any manufacturing technique that leaves a portion of the stent outside the elastic material of the valve body. Further, the invention includes any prosthetic valve in which the prosthetic valve can be implanted without sutures or pins or the like piercing the elastic material of the valve body. The invention is not limited to any of the specific features described herein, but includes all variations thereof within the scope of the appended claims.

What is claimed is:

1. A valve comprising:

a polymer valve body;

a stent, a first portion of the stent being embedded in the valve body and a second portion of the stent being outside he valve body, and a sewing ring coupled to the second portion of the stent.

2. The valve of claim 1 wherein the sewing ring is coupled to the second portion of the stent with sutures.

3. The valve of claim 1 wherein the sewing ring is coupled to the second portion of the stent with cloth.

4. The valve of claim 1 further comprising a coupling element coupled to the second portion of the stent; and wherein the sewing ring comprises sewing ring fabric; and the sewing ring is coupled to the coupling element by wrapping the sewing ring fabric around the coupling element.

5. The valve of claim 1 wherein the valve body comprises an embedding layer for embedding the first portion of the stent.

6. The valve of claim 5 wherein the embedding layer comprises a first portion for embedding a peak of the stent; and a second portion for embedding a base of the stent.

7. The valve of claim 1 wherein the valve body comprises silicone.

8. The valve of claim 1 wherein the stent is insert molded into the valve body.

9. The valve of claim 1 wherein the valve body comprises molded features that mechanically capture the stent.

10. A valve comprising:

an elastic valve body having a plurality of flexible leaflets;

a stent comprising a first portion embedded in the valve body and a second portion outside the valve body, a sewing ring, and a coupling connecting the sewing ring to the stent.

11. A valve comprising:

a polymer valve body having a plurality of flexible leaflets;

a unitary stent, a first portion of the stent being embedded in the valve body and a second portion of the stent being outside the valve body, a sewing ring; and a coupling for joining the sewing ring to the stent.

* * * * *